United States Patent [19]
Oden

[11] Patent Number: 5,342,201
[45] Date of Patent: Aug. 30, 1994

[54] METHOD OF MANUFACTURING CERAMIC ARTIFICAL TOOTH RESTORATIONS

[75] Inventor: Agneta Oden, Stocksund, Sweden

[73] Assignee: Sandvik AB, Sandviken, Sweden

[21] Appl. No.: 79,607

[22] Filed: Jun. 22, 1993

[30] Foreign Application Priority Data

Jun. 23, 1992 [SE] Sweden ............... 9201927-2

[51] Int. Cl.$^5$ ............... A61C 5/10; A61C 5/08
[52] U.S. Cl. ............... 433/223; 433/218
[58] Field of Search ............ 433/223, 218, 213, 202.1, 433/226, 228.1, 222.1

[56] References Cited

U.S. PATENT DOCUMENTS

| | | | |
|---|---|---|---|
| 4,411,626 | 10/1983 | Becker et al. | 433/223 |
| 4,478,580 | 10/1984 | Barrut | 433/223 |
| 4,661,071 | 4/1987 | Bell et al. | 433/223 |
| 4,937,928 | 7/1990 | van der Zel | 29/160.6 |
| 5,080,589 | 1/1992 | Odén et al. | 433/202.1 |
| 5,106,303 | 4/1992 | Odén et al. | 433/223 |
| 5,217,375 | 6/1993 | Odén et al. | 433/218 |

FOREIGN PATENT DOCUMENTS

0241384 10/1987 European Pat. Off. ............ 433/223

*Primary Examiner*—Paul J. Hirsch
*Assistant Examiner*—Cindy A. Cherichetti
*Attorney, Agent, or Firm*—Burns, Doane, Swecker & Mathis

[57] ABSTRACT

There is disclosed a method of manufacturing artificial tooth restorations for natural teeth or implants comprising a ceramic densely sintered, high-strength individual core B with dental porcelain A by powder metallurgical manufacturing methods. The inner surface I of the core B, which will fit against one or more prepared tooth surfaces P or artificial abutments, is manufactured by forming a ceramic powder mixture against a surface of a body at which this mentioned surface is manufactured by registering the surfaces of the prepared teeth or artificial abutments and their mutual relationship with a three-dimensional optical or mechanical reading method directly in the mouth or on a model of, e.g., plaster, after which the registered surfaces are reproduced in an enlarged size, e.g., with a computer-controlled milling machine. The amount of enlargement is calculated from the shrinkage of the ceramic material during sintering to full density and considering the gap for cement.

8 Claims, 5 Drawing Sheets

METHOD OF MANUFACTURING CERAMIC ARTIFICAL TOOTH RESTORATIONS

BACKGROUND OF THE INVENTION

This invention relates to powder metallurgical manufacturing methods for making accurately shaped artificial tooth restorations having an individually manufactured core of a densely sintered, high-strength ceramic material, which fits against prepared tooth surfaces or artificial abutments. On these cores, dental porcelain can be fired to form tooth crowns, inlays, veneers or bridges.

U.S. Pat. No. 5,080,589 discloses a method of manufacturing copings of densely sintered, high-strength ceramic material where the sintering shrinkage is considered. According to this patent, the copings are premanufactured which means that they have been sized before sintering to compensate for shrinkage.

U.S. Pat. No. 5,106,303 and Swedish Patent 469,057 disclose manufacturing of inlays, onlay crowns and veneers of densely sintered, high-strength ceramic material by copy milling a green, a presintered or sintered body from an impression of the prepared tooth surface and considering the sintering shrinkage.

OBJECTS AND SUMMARY OF THE INVENTION

It is an object of this invention to avoid or alleviate the problems of the prior art.

It is further an object of this invention to provide a rational manufacturing technique for manufacturing tooth crowns, inlays, veneers or bridges (collectively, "artificial tooth restorations") of densely sintered, high-strength ceramic material by using modern powder metallurgical and reading techniques.

In one aspect of the invention there is provided a method for making artificial tooth restorations comprising a ceramic and comprising a densely sintered, high-strength core and dental porcelain atop the core comprising:

(a) registering the surfaces of a tooth to be restored or artificial abutments and their mutual relationship with a three-dimensional optical or mechanical reading method directly in the mouth or a model thereof;

(b) reproducing the registered surfaces in a body by a computer-controlled milling machine at a size enlarged to compensate for shrinkage of the ceramic material to be used for the artificial tooth restoration during sintering and for any gap required for cement;

(c) forming a ceramic powder mixture against the reproduced surfaces to form artificial moth restoration precursors having inner surfaces which will fit against the said surfaces of a tooth to be restored or artificial abutments;

(d) sintering the said artificial tooth restorations; and (e) applying a dental porcelain to the outer surface of the core.

In another aspect of the invention there is provided a method for making artificial tooth restorations comprising a ceramic and comprising a densely sintered, high-strength core comprising;

(a) registering the surfaces of a tooth to be restored or artificial abutments and their mutual relationship with a three-dimensional optical or mechanical reading method directly in the mouth or a model thereof;

(b) reproducing the registered surfaces in a body by a computer-controlled milling machine at a size enlarged to compensate for shrinkage of the ceramic material to be used for the artificial tooth restoration during sintering and for any gap required for cement;

(c) forming a ceramic powder mixture against the reproduced surfaces to form artificial tooth restoration precursors having inner surfaces which will fit against the said surfaces of a tooth to be restored or artificial abutments; and (d) sintering the said artificial tooth restorations.

BRIEF DESCRIPTION OF THE DRAWINGS

FIG. 2 shows a cross-section of a bridge, which is cemented on two supporting teeth. These supporting teeth can have a vital abutment $U_1$ or an artificial abutment $U_2$ manufactured of a dental alloy, ceramic material or a strengthened polymer. The bridge in FIG. 2 contains two artificial dental crowns according to FIG. 1 with a pontic V between as replacement for a lost tooth. The bridge contains a core B having dental porcelain A.

In FIG. 3a, F is a tube, $G_1$ is a plate with a cylinder G, which fits into F. H is a cylinder, which also fits into F. H, F, E, G and $G_1$ can be made of, e.g., metallic material. E is made of a viscous elastic material as well as J and X, which are impressions of $K_2$, M is a cavity with space for ceramic powder. $K_1$ has been placed in X and $P_k$ is the force with which H is pressed against G.

FIG. 6 shows $N_1$ and $N_2$ placed in the fixture f. X is a tool made in a rubber material and $M_1$ is a cavity.

DETAILED DESCRIPTION OF THE PREFERRED EMBODIMENTS OF THE INVENTION

Figure 1A:
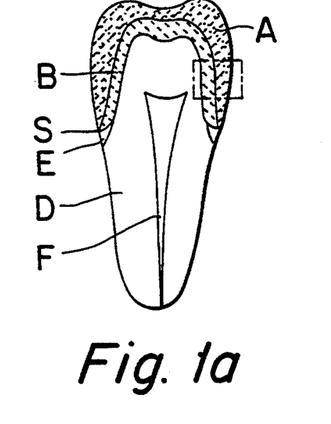
FIGS. 1a–1e show cross-sections of natural teeth, one with an artificial tooth crown (FIG. 1a), one with an inlay (FIG. 1b), and one with a veneer (FIG. 1c) as well as partial cross-section of FIGS. 1a and 1b (FIG. 1d) and of FIG. 1c (FIG. 1e). In these figures, A=dental porcelain, B=core of densely sintered ceramic, Y=the outer surface of the core, I=the inner surface of the core, C=cement, P=the prepared surface of the tooth, S=the preparation border, E=enamel, D=dentin, and F=pulp.
Figure 1B:
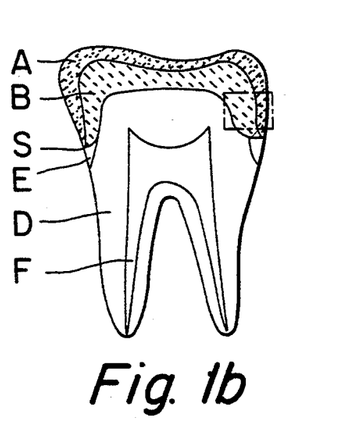
Figure 1C:
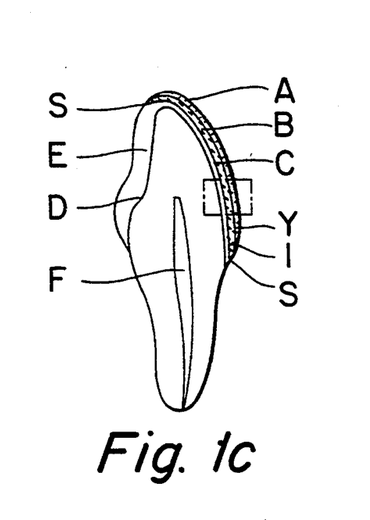
Figure 1D:
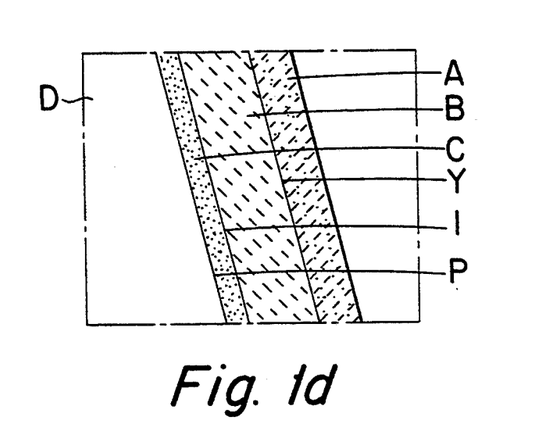
Figure 1E:
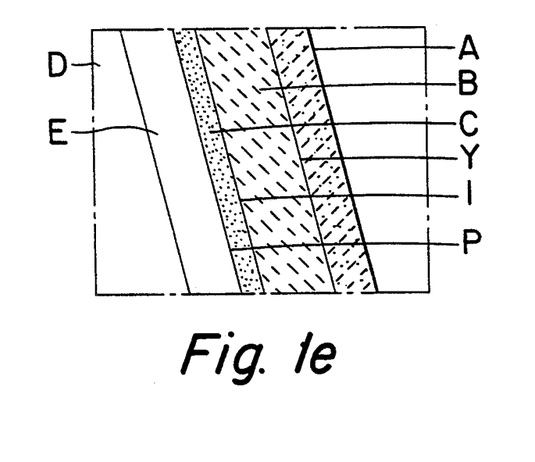
Figure 2:
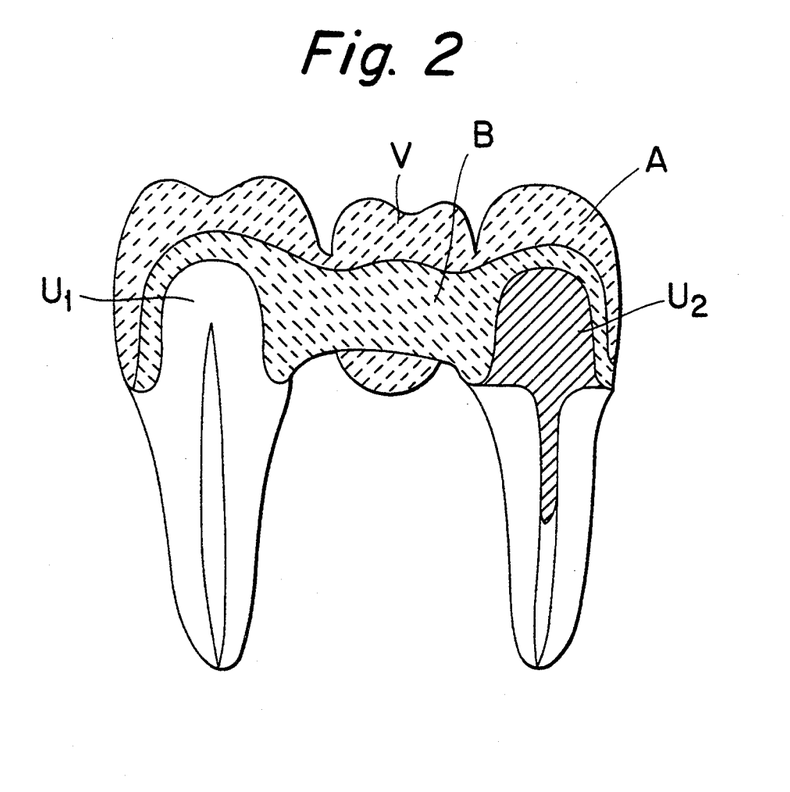

As can be seen from FIGS. 1 and 2, artificial tooth restorations such as crowns, inlays, veneers or bridges are made as a core of densely sintered ceramic B with dental porcelain fired to the surface A. The tooth restorations are fixed to the prepared surfaces P by, e.g., cementing, as well as the bridge to the abutments $U_1$ and $U_2$. The thin layer of cement C connects the prepared cavity walls P with that part of the surface of the inner surface of the core I, which has been made so that this surface D fits with great precision to the prepared surface P. On the outer surface Y of the core B dental porcelain can be fired. The layer of cement can have a thickness < 100 μm, preferably 25-50 μm. The cementing of the restorations can be made with, e.g., zinc phosphate cement, glass-ionomer cement or a resin cement A as known in the art. In the last case, it can be an advantage to silane treat the inner surfaces I of the cores of the constructions, which will be joined with the prepared surfaces P of the tooth structure as well as it also can be advantageous to etch and treat the prepared surfaces P with a bonding resin before the cementation. A bridge can contain more supporting teeth and also more pontics in between. The supporting teeth can also be prepared for inlays or veneers. Veneers can be made both buccaly and lingually. The supporting teeth can also be implants with artificial abutments.

The ceramic powder can be made by several methods well-known to the skilled artisan. Traditional powder metallurgical technique can be used, where the different components are mixed and ground under dry or wet conditions with water or an inorganic solvent, e.g., alcohols, as a grinding liquid. To the ceramic slurry, lubricants or other organic binders depending on the choice of forming method are added, when needed at a suitable time in the process.

The ceramic base material of the core preferably comprises one or several biocompatible oxides, with additives of carbides and nitrides with or without binders. Examples of biocompatible oxides, which can form the base matrix for the ceramic body, are $Al_2O_3$, $TiO_2$, MgO, $ZrO_2$ and $ZrO_2$ with additives of smaller amounts of up to 10 mole % of $Y_2O_3$ or MgO (partly or totally stabilized $ZrO_2$). Additives can be present as particles with a size of < 25 μm, preferably < 10 μm, and/or as whiskers (hair-shaped single crystals) with a length of > 10 μm, preferably > 25 μm, and a length to diameter ratio > 5, preferably > 10, and/or fibers (polycrystalline) with a diameter > 10 μm and/or single crystal platelets with an approximate diameter of 5-50 μm and a thickness of 1-10 μm. The amount of whiskers, fibers and/or platelets should not exceed 60 volume %.

In a preferred embodiment, the ceramic material comprises > 50% $Al_2O_3$ with additives of conventional sintering aids. In order to increase the strength < 25 weight %, preferably 3-12 weight %, of $ZrO_2$, and/or 5-40 weight %, preferably 10-30 weight %, of SiC-, TiN- or ZrN-whiskers can be added. It is important that the ceramic material is sintered to closed porosity, which for an oxide material means at least 95% of theoretical density, but in order to ensure good mechanical strength, the material should preferably have a density over 98% with densities over 99.5% giving the best strength.

In order to get a suitable color for the core B, colored components can be chosen. Additives, e.g., 0.1-1 weight % of TiN and/or ZrN, will give $Al_2O_3$-based cores a faint yellow shade. $Fe_2O_3$ gives a yellow-brown shade and $MnO_2$ gives a rose-colored shade. Of course, additives which give non-aesthetic effects should not be used.

Figure 3A:
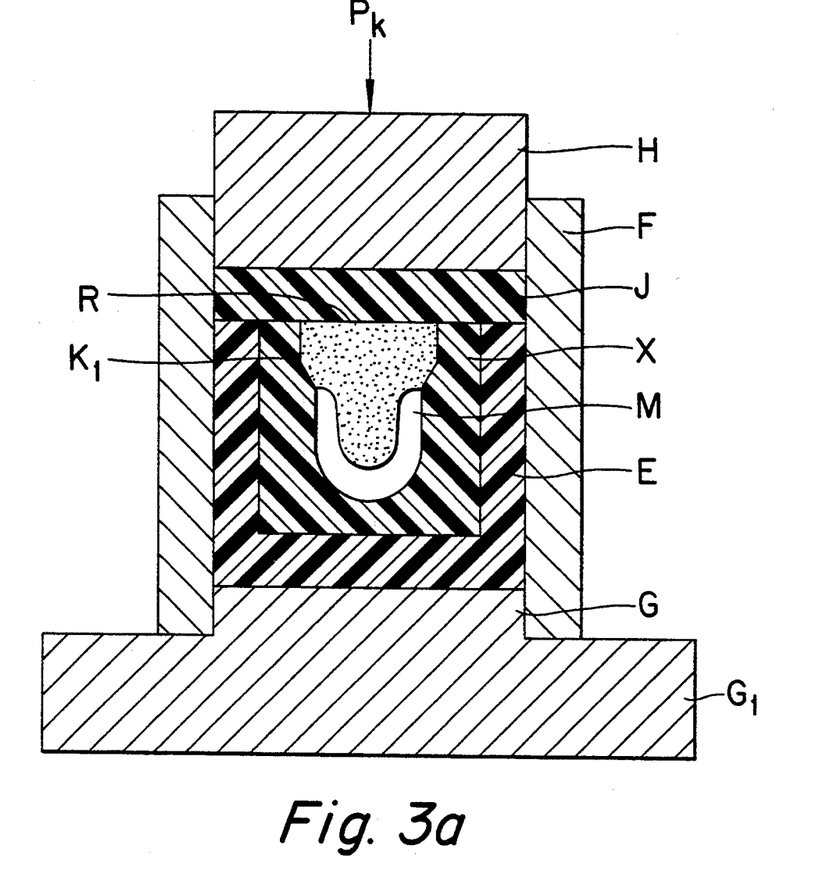
FIG. 3a shows a cross-section of an example of a press for individual cores for tooth crowns.
Figure 3B:
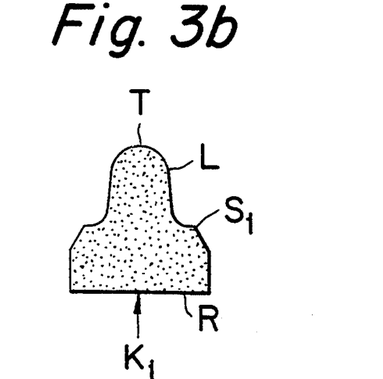
FIG. 3b is a cross-section of a model $K_1$ of a preparation for a tooth crown enlarged considering the sintering shrinkage, $S_1$ is the preparation border, T is the top of the model, R is the bottom of the model and L is the enlarged surface of the preparation surface P.

According to the present invention, artificial ceramic tooth crowns, inlays, veneers and bridges can now be made from a ready-to-press powder with additions of lubricants and/or other organic binders. When manufacturing the core of an individual tooth crown, the powder is compacted against the body $K_1$ to form a core, which after sintering to full density fits to the prepared surface with a desired wall thickness. When manufacturing the enlarged model $K_1$, the sintering shrinkage has to be considered. The surface L must be enlarged in order to have the desired inner geometrical shape I of the green body which fits against the prepared surface P after the subsequent sintering process. The desired shape of the gap between the tooth crown and the prepared tooth for cementing the crown to the prepared tooth must also be considered. The size of this gap can be calculated, e.g., to be as small as possible, at the preparation border.

Figure 3C:
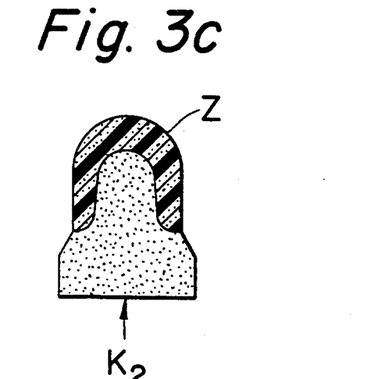
FIG. 3c shows a cross-section of a model $K_2$ which consists of $K_1$ with a coping of, e.g., wax, and Z is the outer surface of this coping.

The cores of the tooth crowns are manufactured by cold isostatic compaction, uniaxial pressing, slip casting, pressure casting, injection molding or by compacting the powder in another way, preferably by a cold isostatic technique against a body $K_1$, which is shown in FIG. 3b. $K_1$ has a surface L, which is uniform with the surface P of the prepared tooth, on which the tooth crown or the veneer will fit. The body $K_1$ is manufactured by registering the prepared surface P or an artificial abutment directly in the mouth or from a model, e.g., in plaster, by a three-dimensional mechanical or optical method known to the skilled artisan. The registered surface is reproduced in an enlarged size L, e.g., with a computer-controlled milling machine. The enlargement is calculated from the shrinkage of the ceramic material during sintering to full density. When calculating the shape of $K_1$, the gap for cement is considered. It is important that the preparation border $S_1$ is evident. Below the preparation border $S_1$, that is, between $S_1$ and the bottom R, the body $K_1$ is given such a shape that its surfaces converge to the occlusal part of the preparation. At the bottom R, the outer surface can be, e.g., cylindrical. The body $K_1$ can be manufactured of any suitable material, e.g., metal, graphite, polymers, etc. $K_1$ will have such a size that the inner surface of the green body (the impression of L) after shrinkage during sintering to full density receives the inner surface I which has the desired fit against the prepared tooth surface P or to an artificial abutment. The surface L of the body $K_1$ is manufactured with a computer-controlled milling machine, which enlarges the registered tooth surface, and will, after compacting the powder against this surface L and sintering to full density, give the inner shape of the core I. During compaction, the outer surface Y of the core is formed as follows: A body $K_2$ which is shown in FIG. 3c is milled with a computer-controlled milling machine from registered data from the prepared surface P of the registered tooth or the surface of the artificial abutment. This body $K_2$ is enlarged considering the sintering shrinkage in the same way as the body $K_1$ and with an additional material from the preparation border or just below. $K_2$ contains the outer surface Z. The outer surface Z can be formed by forming a coping any easily moldable material, e.g., wax, or other material which easily can be formed against the body $K_1$. The outer surface Z of this second body $K_2$ or $K_1$ with a coping in, e.g., wax, is used to form the outer shape Y of the core. An impression X is made from the body $K_2$, or $K_1$ with a coping in, e.g., wax, in conventional viscous elastic material, e.g., a silicone. The compaction of the powder can be made with a tool as shown in FIG. 3a. This tool contains the impression X. $K_1$ fits into X from the bottom R to the preparation border S. Between the surface L of $K_1$ and X there is a cavity M. The impression X has such a shape as to fit into a body E, which can contain the viscous elastic material. The body E is placed into a tube F, which is put on G, which is a part of $G_1$. The cylinder H with the same diameter as G is put into the tube F from the top. On top of the body E (which contains the impression X) and below the cylinder H is a lid J made of the same material as E.

The manufacture of an individual core to a tooth crown can be made in the following way. The pressing tool is put together with the tube F on the cylinder G. The body E with the impression X is put into the tube F. Ready-to-press powder is filled into the cavity M and the body $K_1$ is fit into the impression X. $K_1$ fits into the impression X from the preparation border $S_1$ or just below and to the bottom R of the body $K_1$. Finally, the lid J and the cylinder H are placed atop the assembly and the whole tool as shown in FIG. 3a is put into a press, e.g., a uniaxial hydraulic press. During the compaction of the powder, the cylinder H is pressed with the force $P_k$ in the tube F against the cylinder G in contact with the lid J and the powder is compacted against the body $K_1$. After the compaction, the cylinder H, lid J and body $K_1$ are removed as well as the compacted shell which in some cases is attached to $K_1$. The body $K_1$ should not contain any undercuts. The wall thickness of the green body is determined by the amount of powder put into the cavity M. After the pressing, the green body is adjusted at the preparation border $S_1$ and the wall thickness is controlled and adjusted before the sintering to full density. The wall thickness can be 0.5 mm, however, on certain places, wall thicknesses $>0.5$ mm may be needed in order to strengthen marginal ridges or for replacement of removed fillings. These thicknesses, if needed, can be readily determined by the skilled artisan. After sintering to full density, the core B is adjusted against the preparation border S of the plaster model in order to fit the surface I of the core B against the surface P of the prepared tooth or against the artificial abutment. Finally, dental porcelain A can be fired to the core for the manufacture of a tooth crown.

A veneer can be manufactured in the same way as above.

A core B of an inlay can also be manufactured by registering the surface P prepared for an inlay by a three-dimensional mechanical or optical method. The registered tooth surface is reproduced in an enlarged size of a suitable material, e.g., a metal, graphite or a polymer, by, e.g., use of a computer-controlled milling machine which enlarges the preparation. The amount of enlargement is calculated from the shrinkage of the ceramic material during sintering to full density and with a reduction for the cement. An impression X (FIG. 3a) can be manufactured in the same way as for a core of a tooth crown discussed above. Before the manufacturing of the impression X for an inlay, the enlarged preparation is over-filled with, e.g., wax. This enlarged model with the filled preparation cavity is used for the manufacture of the impression X in a conventional viscous elastic material, e.g., a silicone. This impression is placed in a press in the same way as described for FIG. 3a after the ceramic powder has been put in the cavity between the enlarged model and the impression X. After compaction, the green body is removed. In order to be able to remove the green body without destroying it, the preparation must not contain any undercuts. The green body is adjusted against the preparation border and space can be given if dental porcelain will be fired to the outer surfaces of the inlay, that means the surfaces which are not cemented against the prepared surfaces of the tooth. After the sintering of the core, some adjustment by grinding or polishing can be needed.

When manufacturing a bridge, it is important to maintain the mutual relationship after the enlargement. A bridge can be manufactured by starting with the registration of the surfaces of the prepared tooth and the soft tissue in between by a three-dimensional mechanical or optical method. Registration of the mutual relationship of the supporting teeth can be done in the following way. An impression is made with conventional impression technique, e.g., with a silicone impression material. This impression is cast in, e.g., plaster. From this model or directly in the mouth, the prepared teeth and the jaw in between is registered by a three-dimensional mechanical or optical method. The prepared teeth and the tooth free jaw in between are reproduced in an enlarged size with, e.g., a computer-controlled milling machine. The enlargement is calculated from the shrinkage of the ceramic material during sintering to full density and with an additional space for the cement. The material of the enlarged models can again be, e.g., graphite, metal or a polymer.

Figure 4A:
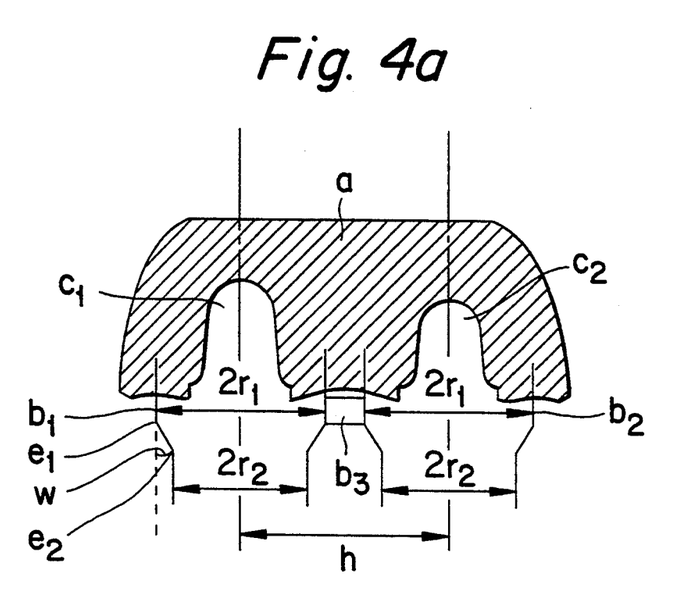
FIG. 4a shows a cross-section of an impression of two supporting teeth prepared for crowns and the gingiva between the teeth. $c_1$ and $c_2$ are the impressions of the preparations of the supporting teeth in a, which is the impression material. $b_1$ and $b_2$ are two parallel tubes firmly united to each other through $b_3$. The inner surfaces of $b_1$ and $b_2$ consist of two cylinder surfaces with radii $r_1$ and $r_2$ (FIG. 4b). They are connected with $e_1$–$e_2$. w is the angle between the parts of $b_1$ and $b_2$ with radius $r_1$ and the surface with the cross-section $e_1$–$e_2$. $q_1$ and $q_2$ (FIG. 4b) are grooves in the part of the tubes $b_1$ and $b_2$ with radius $r_2$. It is the distance between the parallel central axes of $b_1$ and $b_2$.
Figure 4B:
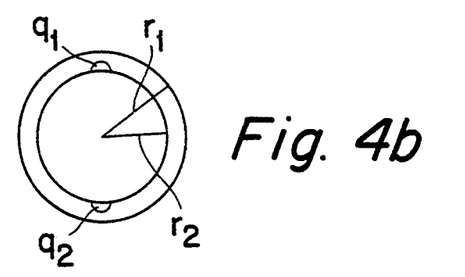
FIGS. 4c and 4d show models $n_1$ and $n_2$, respectively, of $c_1$ and $c_2$ made by pouring model material, e.g., plaster, in the tubes $b_1$ and $b_2$ and $c_1$ and $c_2$.
Figure 4C:
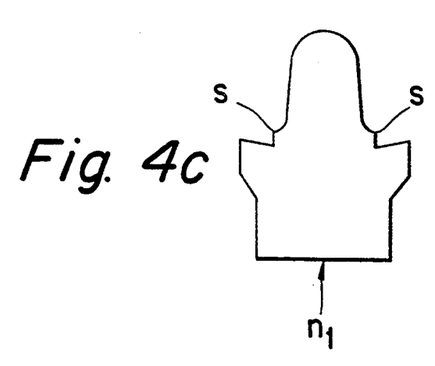
Figure 4D:
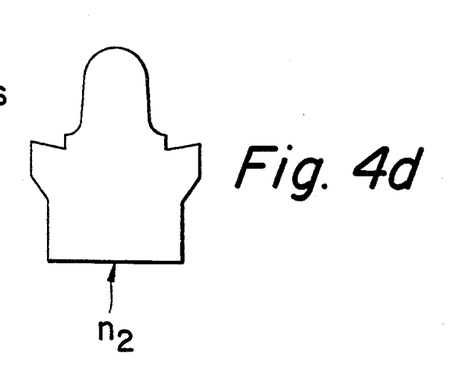
Figure 5A:
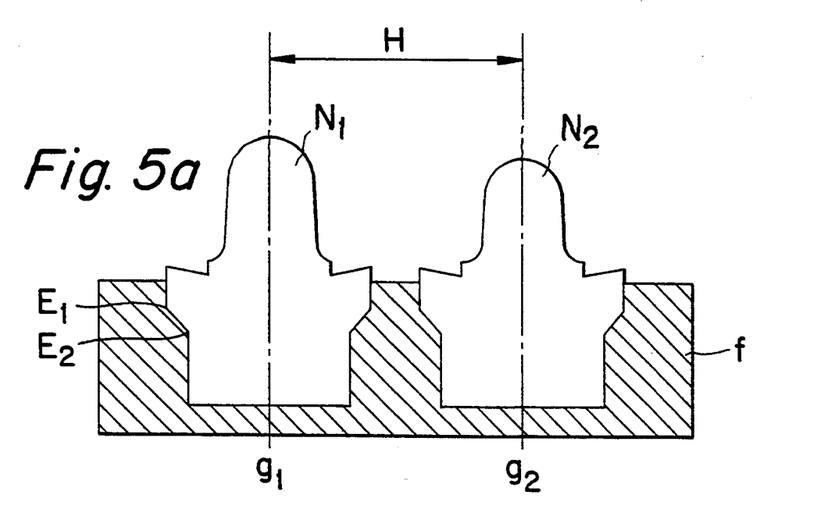
FIG. 5a shows $N_1$ and $N_2$ which are enlarged (compensated for the shrinkage during sintering) models of $n_1$ and $n_2$ in a mixture f with the holes $g_1$ and $g_2$, manufactured so that the distance H between the central axes of $g_1$ and $g_2$ is h when enlarged considering the sintering shrinkage as well as the inner shape of the holes $g_1$ and $g_2$, which are enlarged from the inner surface of the tubes $b_1$ and $b_2$. $Q_1$ and $Q_2$ (FIG. 5b) are enlarged grooves $q_1$ and $q_2$.
Figure 5B:
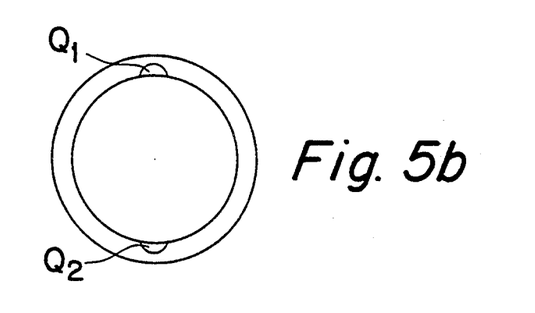
Figure 6:
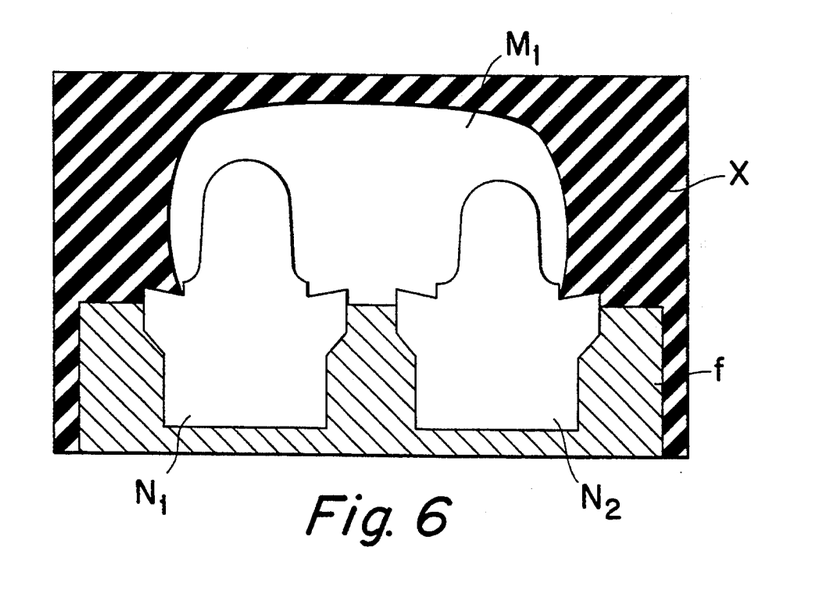

An enlarged model which considers the whole situation can also be made in the following way. An impression as shown in FIG. 4a is made from the supporting teeth and the tissue in between with a conventional impression technique, e.g., with an impression material in, e.g., a silicone material a. FIG. 4a shows a cross-section of an impression. The tubes $b_1$ and $b_2$ are pressed into the impression material a. In order not to deform the impression of the preparations, that part of the tubes pressed into the impression material can, e.g., have a chamfered edge. The tubes can also be fixed to the impression with, e.g., sticky wax. The tubes $b_1$ and $b_2$ can, e.g., have elliptic or circular cross-section with grooves $q_1$ and $q_2$ in the longitudinal axis in the internal surfaces of the tubes, and a step $e_1$–$e_2$, is clear from a cross-section parallel with the longitudinal axes. The tubes $b_1$ and $b_2$ have parallel longitudinal axes and surround the impressions $c_1$ and $c_2$ of the preparations of the supporting teeth in the impression material a. The tubes $b_1$ and $b_2$ are fixed to each other with $b_3$. The impressions $c_1$ and $c_2$ are poured out in, e.g., plaster, which gives the models $n_1$ and $n_2$ shown in FIGS. 4c and $d$. The models $n_1$ and $n_2$ are registered with a three-dimensional mechanical or optical method and are reproduced in an enlarged size with, e.g., a computer-controlled milling machine. The amount of enlargement is calculated from the shrinkage of the ceramic material during sintering to full density and with an additional space for the cement above the preparation border $S_1$ of the models $N_1$ and $N_2$. The material can again be, e.g., a metal, graphite or a polymer. These enlarged models $N_1$ and $N_2$ are put into a fixture f as shown in FIG. 5a. The fixture f contains a plate of a suitable material, e.g., a metal, which has two holes $g_1$ and $g_2$. These holes have a geometry which is uniform with the internal surface of the tubes $b_1$ and $b_2$ and enlarged with the same enlargement factor considering the sintering shrinkage for the current ceramic powder. The distance H between the longitudinal axes of the holes is enlarged considering the sintering shrinkage of the ceramic material. By placing the enlarged models $N_1$ and $N_2$ in the fixture f an enlarged model of the prepared supporting teeth and their mutual relationship is made. The step $E_1$–$E_2$ and the grooves $Q_1$ and $Q_2$ and the distance H give the mutual relationship of the enlarged preparations. The manufacturing of the tool for compacting the ceramic powder to the bridge is made in a similar way as is shown in FIG. 3a. An impression X is made which gives space for powder to a beam which connects the copings, which after the compaction will fit the enlarged preparations $N_1$ and $N_2$. FIG. 6 is an outline figure of the impression X. In FIG. 6, the models $N_1$ and $N_2$ put in the fixture f are placed in the impression X, manufactured in the same way as has been described for cores of single tooth crowns. In the empty space $M_1$, which surrounds $N_1$ and $N_2$, ceramic powder is placed and the tool is put in a pressing tool according to FIG. 3 and a compacting pressure $P_k$ is applied. The ceramic powder will be compacted against $N_1$ and $N_2$ and against the part of the fixture, which is situated between $N_1$ and $N_2$. The green body is removed and the copings are adjusted at the preparation border and where the wall thickness needs reduction. The beam can be formed with, e.g., a milling cutter in a hand piece of a dental technician in order to give it a suitable form as a substructure of pontics. The core is sintered to full density. After sintering, some adjustments may be needed before the firing of dental porcelain to the core to have a bridge according to FIG. 2.

The manufacturing of a bridge and the mutual relationship of the supporting teeth can be maintained after the enlargement in many other ways, e.g., before the impression a is cast, markers are placed in the impression in such a way that they give impressions in the different parts (the supporting teeth and the jaw in between) into which the plaster model is divided by sawing. The impressions of the markers in combination with enlarged markers can be used to have the mutual relationship of the supporting teeth after the enlargement.

A bridge can also be manufactured, which is based on supporting teeth with preparations for a veneer on the buccal surface or a preparation on the lingual surface for a lingual plate. The manufacture of such a bridge can be made in the same way as has been described for a bridge with supporting teeth prepared for full crowns.

A bridge can also be made for supporting teeth prepared for inlays. In order to have the mutual relationship between the supporting teeth in the enlarged model considering the sintering shrinkage, the manufacture of compaction tool and the compaction are made in the same way as described for a bridge with supporting teeth prepared for full crowns. The supporting teeth can have different types of preparations.

A bridge based on supporting teeth prepared for inlays can also be made in densely sintered ceramic material by starting from, e.g., a plaster model of the prepared teeth and the jaw between. A beam can be made by using a light hardened polymer filled into the inlay preparations and connecting the preparations of the bridge. Before the hardening of the polymer, it is given such a shape that the inlays and the beam between have the desired form. After the light hardening of the polymer bridge, it is removed and is registered by a three-dimensional mechanical or optical method and reproduced in an enlarged size to a green body or a presintered ceramic body with, e.g., a computer-controlled milling machine. The enlargement is calculated from the shrinkage of the ceramic material during sintering to full density.

Another way of manufacturing a densely sintered shell, which after sintering to full density fits to a prepared tooth, is to make an impression of the enlarged body $K_1$ considering the sintering shrinkage and an additional space for the cement according to FIG. 3a. This impression is cast in plaster and a model $K_3$ in plaster is obtained from $K_1$. An impression X is made according to FIG. 3a. Ceramic powder is compacted against the model $K_3$ with, e.g., the compaction tool described in FIG. 3a. The green body is presintered on the plaster model. Alumina is presintered at 800° C.–1100° C. During the presintering water is released from the plaster, which shrinks about 15%. The ceramic material shrinks much less and the presintered core can easily be removed, adjusted and sintered to full density.

Further, another way of manufacturing a densely sintered shell, which after sintering to full density fits on a prepared tooth, is to make a slurry of ceramic powder mixed and ground under wet conditions with water or an organic solvent, e.g., an alcohol, as a grinding liquid. To the ceramic slurry, lubricants or other organic binders are added. On the enlarged plaster model $K_3$ of the prepared tooth, the slurry of the ceramic powder is placed in some way, e.g., with a brush from the preparation border $S_1$ to the top T. The plaster model of $K_1$ ($K_3$) can also be dipped into a slurry of the ceramic powder. In order to have an optimal compaction of the powder, a suction cup can be applied to the bottom surface R and by a suction cup a negative pressure is applied during the dipping of the body $K_3$ into the slurry as described in U.S. patent application Ser. No. 07/828,952, the disclosure of which is hereby incorporated by reference. The ceramic particles will be packed against the plaster model when this model absorbs the water from the slurry. In this way, the ceramic powder is compacted against the plaster model and the body compacted in this way can be adjusted at the preparation border $S_1$ and adjusted to desired shape and shell thickness of the core. The green body is presintered on the plaster model. The presintered body will be too big for the plaster model and can be removed for any adjustment and sintering to full density. Instead of plaster, other porous materials can be used provided that they can be used provided that they can be used as sintering support during the presintering.

Bridges can be manufactured with the above described slip casting method by making an impression from $N_1$ and $N_2$ in the fixture f, FIG. 5a, and cast in, e.g., plaster. Before the impression is made, a support for the slurry to make the substructure for the pontics is built up with, e.g., wax, on the fixture between $N_1$ and $N_2$. An impression is made of the fixture with the support $N_1$ and $N_2$ for the pontics, which is cast in plaster. The plaster model is fixed to a plate in some ceramic material and is divided into three parts, $N_1$, pontic and $N_2$. The three parts have the same mutual relationship as before the separation. Against the plaster model, a slurry is place in the same manner as was described for cores for single tooth crowns. The separated and fixed plaster model with the ceramic slurry is presintered and the presintered bridge core can, if needed, be adjusted before the sintering to full density.

Another way of manufacturing a core of a bridge is to compact ceramic powder with a tool shown in FIG. 6 against $N_1$ and $N_2$ in the fixture f according to FIG. 5a or against a plaster model according to FIG. 5a fixed and separated into three parts. The tool is placed in a compaction tool similar to that shown in FIG. 3a after the ceramic powder has been placed into $M_1$. The green body manufactured in this way is adjusted before the presintering. After presintering, the body can have any adjustment before the sintering to full density in a known way.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method for making artificial tooth restorations comprising a ceramic and comprising a densely sintered, high-strength core and dental porcelain atop the core comprising:
   (a) registering the surfaces of a tooth to be restored or artificial abutments and their mutual relationship with a three-dimensional optical or mechanical reading method directly in the mouth or a model thereof;
   (b) reproducing the registered surfaces in a body by a computer-controlled milling machine at a size enlarged to compensate for shrinkage of the ceramic material to be used for the artificial tooth restoration during sintering and for any gap required for cement;
   (c) forming a ceramic powder mixture against the reproduced surfaces to form artificial tooth restoration precursors having inner surfaces which will fit against the said surfaces of a tooth to be restored or artificial abutments;
   (d) sintering the said artificial tooth restorations; and
   (e) applying a dental porcelain to the outer surface of the core.

2. The method of claim 1 wherein the outer surface of the core is dry pressed close to desired size against the enlarged reproductions using an impression in some viscous elastic material.

3. The method of claim 1 wherein the core is made by a dry pressing against a plaster model of the enlarged reproductions, after which the core is presintered on the plaster model.

4. The method of claim 1 wherein the core is manufactured by slip casting against a plaster model of the enlarged reproductions, after which the core is presintered on the plaster model.

5. The method of claim 1 wherein the ceramic material of the core has a relative density of $>99\%$.

6. The method of claim 5 wherein the ceramic material of the core is based on one more of the oxides $Al_2O_3$, $TiO_2$, $MgO$, $ZrO_2$ or $ZrO_2$ with up to 25 mole % $Y_2O_3$ or $MgO$.

7. The method of claim 5 wherein the core material also comprises whiskers and/or particles of SiC, TiN, $ZrO_2$ and/or ZrN.

8. A method for making artificial tooth restorations comprising a ceramic and comprising a densely sintered, high-strength core comprising;
   (a) registering the surfaces of a tooth to be restored or artificial abutments and their mutual relationship with a three-dimensional optical or mechanical reading method directly in the mouth or a model thereof;
   (b) reproducing the registered surfaces in a body by a computer-controlled milling machine at a size enlarged to compensate for shrinkage of the ceramic material to be used for the artificial tooth restoration during sintering and for any gap required for cement;
   (c) forming a ceramic powder mixture against the reproduced surfaces to form artificial tooth restoration precursors having inner surfaces which will fit against the said surfaces of a tooth to be restored or artificial abutments; and
   (d) sintering the said artificial tooth restorations.

* * * * *